(12) United States Patent
Takahashi et al.

(10) Patent No.: US 10,352,760 B2
(45) Date of Patent: Jul. 16, 2019

(54) DEVICE AND SYSTEM FOR DETECTING MALFUNCTION OF ROTATING MACHINE

(71) Applicant: Kobe Steel, Ltd., Hyogo (JP)

(72) Inventors: Eiji Takahashi, Kobe (JP); Kaname Araki, Kobe (JP); Shugo Takaki, Takasago (JP); Masato Hayashi, Takasago (JP)

(73) Assignee: Kobe Steel, Ltd., Hyogo (JP)

( * ) Notice: Subject to any disclaimer, the term of this patent is extended or adjusted under 35 U.S.C. 154(b) by 213 days.

(21) Appl. No.: 15/380,234

(22) Filed: Dec. 15, 2016

(65) Prior Publication Data
US 2017/0219421 A1 Aug. 3, 2017

(30) Foreign Application Priority Data

Feb. 2, 2016 (JP) .................................. 2016-018062

(51) Int. Cl.
| | |
|---|---|
| *G01H 1/00* | (2006.01) |
| *G01N 29/06* | (2006.01) |
| *G01N 29/14* | (2006.01) |
| *G01N 29/22* | (2006.01) |
| *G01N 29/38* | (2006.01) |

(Continued)

(52) U.S. Cl.
CPC ......... *G01H 1/003* (2013.01); *G01N 29/0618* (2013.01); *G01N 29/0645* (2013.01); *G01N 29/14* (2013.01); *G01N 29/226* (2013.01); *G01N 29/38* (2013.01); *G01N 29/4445* (2013.01); *G01N 29/4454* (2013.01); *G01N 29/46* (2013.01); *G01N 2291/2693* (2013.01)

(58) Field of Classification Search
CPC ............... G01H 1/003; G01N 29/0618; G01N 29/0645; G01N 29/14; G01N 29/226; G01N 29/38
USPC .......................................................... 73/579
See application file for complete search history.

(56) References Cited

U.S. PATENT DOCUMENTS

| | | | |
|---|---|---|---|
| 5,965,819 | A | 10/1999 | Piety et al. |
| 6,094,989 | A | 8/2000 | Twerdochlib |

(Continued)

FOREIGN PATENT DOCUMENTS

| | | |
|---|---|---|
| CN | 102272562 A | 12/2011 |
| CN | 103688144 A | 3/2014 |

(Continued)

*Primary Examiner* — Tarun Sinha
(74) *Attorney, Agent, or Firm* — Studebaker & Brackett PC

(57) ABSTRACT

Provided is a device for detecting a malfunction of a rotating machine, the device being able to early detect the malfunction and to have a reduced size. The device includes a detecting unit for detecting vibration of the machine, sampling a signal indicative of the vibration with a predetermined sampling frequency, and outputting, at a time at intervals of a predetermined period, a plurality of the sampled data detected within the predetermined period, a storage for storing the plurality of the sampled data, a frequency analyzer for analyzing the frequency of the plurality of the sampled data, a determination unit for performing a primary determination based on the result of the analysis, a display unit for displaying the result of the analysis in chronological order and in real time, and a communication unit for transmitting the plurality of the sampled data to an information-processing device for performing a secondary determination.

11 Claims, 4 Drawing Sheets

(51) Int. Cl.
*G01N 29/44* (2006.01)
*G01N 29/46* (2006.01)

(56) References Cited

U.S. PATENT DOCUMENTS

| | | | |
|---|---|---|---|
| 6,862,517 B2 * | 3/2005 | Galtier | G01L 23/225 |
| | | | 123/406.16 |
| 8,942,426 B2 * | 1/2015 | Bar-Am | B61K 9/08 |
| | | | 104/242 |
| 2006/0224293 A1 * | 10/2006 | Kawazoe | B62D 6/00 |
| | | | 701/70 |
| 2009/0228525 A1 * | 9/2009 | Fridrich | G06Q 10/10 |
| 2010/0076692 A1 * | 3/2010 | Vock | A43B 3/0005 |
| | | | 702/19 |
| 2011/0209546 A1 | 9/2011 | Seuthe | |
| 2012/0072136 A1 * | 3/2012 | Hedin | G01H 1/003 |
| | | | 702/56 |
| 2014/0142872 A1 | 5/2014 | Hedin | |
| 2017/0212085 A1 * | 7/2017 | Kajita | G01M 99/00 |

FOREIGN PATENT DOCUMENTS

JP    H08-166330 A    6/1996
WO    2013/009258 A1    1/2013

* cited by examiner

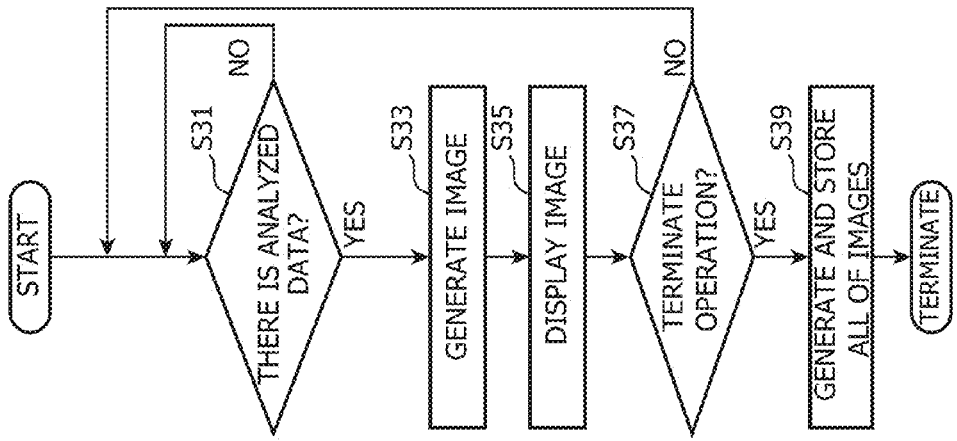
F I G. 4A
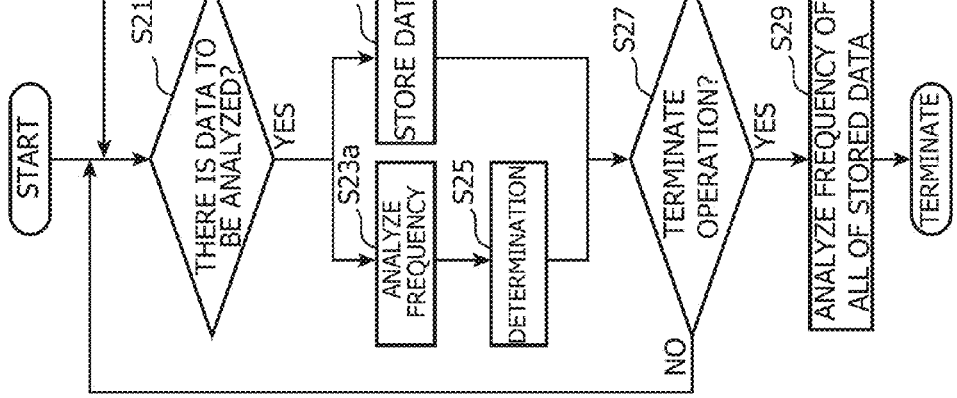
F I G. 4B
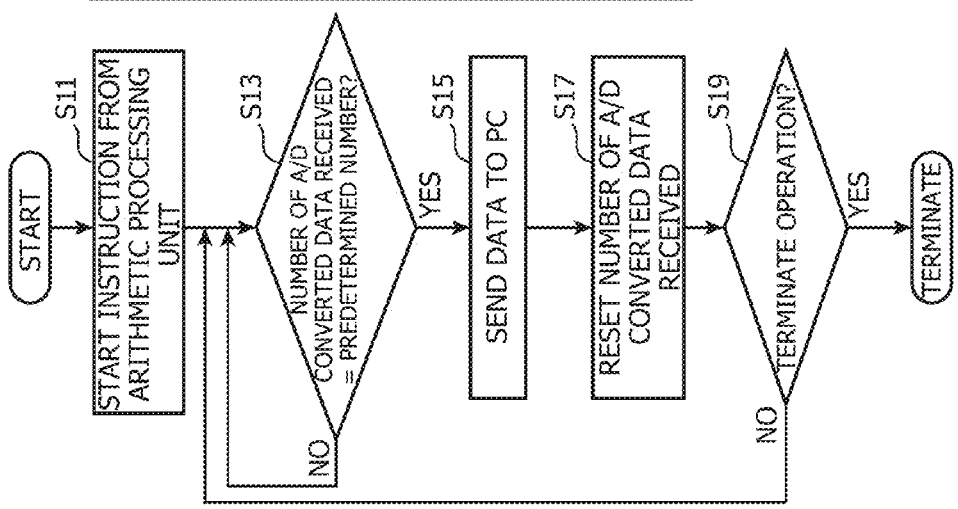
F I G. 4C

DEVICE AND SYSTEM FOR DETECTING MALFUNCTION OF ROTATING MACHINE

BACKGROUND OF THE INVENTION

Field of the Invention

The present invention relates to a device and a system for suitably detecting a malfunction of a rotating machine such as, for example, a malfunction of a rotor.

Description of the Related Art

During the operation of a rotating machine such as a turbine and a compressor, a rotor usually rotates at high speed. Later detection of a malfunction such as damage of the rotor, for example, may lead to increased severity of the malfunction. To make matters worse, the malfunction may result in shutdown of the rotating machine. Thus, it is desirable to early detect and notify such malfunction of a rotating machine.

For example, a device for diagnosing abnormal slide, described in JP 8-166330, uses an AE (acoustic emission) sensor to detect an AE signal from a rotating machine; analyzes the frequency of the detected AE signal to determine the presence, location, and degree of abnormal slide; and displays the result of the determination.

Problems to be Solved by the Invention

If an operator can comprehend the operating states of a rotating machine at respective times, the operator can recognize a change in operation states of the rotating machine over time, thereby allowing earlier detection of a malfunction of the rotating machine. Although the conventional device described in JP 8-166330 displays the results of determination of the presence, location, and degree of abnormal slide, the device does not display time-dependent trends in the results. Thus, the conventional device can identify, for example, the presence of a malfunction of a rotating machine but is difficult to early detect the malfunction.

Another problem is encountered in detecting a malfunction of a rotating machine. Detectors for detecting a malfunction of a rotating machine also include stethoscopes as well as devices for detecting a malfunction of a rotating machine. For example, when there is no need to fixedly install a device for detecting a malfunction of a rotating machine (for example, in a case in which a new rotating machine or an overhauled rotating machine is inspected for a malfunction only when the machine is tested); when there is no space installation for a device for detecting a malfunction of a rotating machine in the installed location of a rotating machine; or when a rotating machine is installed outside, and thus no electrical outlet is available, a stethoscope is used to detect a malfunction of a rotating machine.

However, considerable skill is required to use a stethoscope to detect a malfunction of a rotating machine. Thus, there is a need for a portable device for detecting a malfunction of a rotating machine, the device being enabled to be used in place of a stethoscope or in combination with a stethoscope to detect a malfunction of a rotating machine. To achieve this, it is necessary to reduce the size of a device for detecting a malfunction of a rotating machine.

The present invention has been developed in view of the foregoing. It is an object of the present invention to provide a device for detecting a malfunction of a rotating machine, the device being able to early detect a malfunction of a rotating machine and to have a reduced size, and a system for detecting a malfunction of a rotating machine, the system including such device.

Means of Solving the Problems

A first aspect of the present invention is a device for detecting a malfunction of a rotating machine, the device including a detecting unit for sampling and detecting vibration of the rotating machine with a predetermined sampling frequency, and outputting, at a time at intervals of a predetermined period, a plurality of the sampled data detected within the predetermined period; a storage for storing the plurality of the sampled data outputted by the detecting unit; a frequency analyzer for analyzing the frequency of the plurality of the sampled data outputted by the detecting unit; a determination unit for performing a primary determination based on the result of the frequency analysis by the frequency analyzer; a display unit for displaying the result of the frequency analysis by the frequency analyzer in chronological order and in real time; and a transmitting unit for transmitting, to an information-processing device for performing a secondary determination, the plurality of the sampled data outputted by the detecting unit.

The detecting unit outputs, at a time at intervals of a predetermined period, a plurality of the sampled data detected within the predetermined period. The detecting unit may output, at a time at intervals of a predetermined period, all of the plurality of the sampled data detected within the predetermined period or may output part of the plurality of the sampled data at a time.

The device for detecting a malfunction of a rotating machine in the first aspect of the present invention displays, in chronological order and in real time, the result of frequency analysis of the data created by sampling and detecting vibration of the rotating machine. In other words, the device displays, substantially in real time, the operating states of the rotating machine at respective times, which allows an operator to recognize a change in operation states of the rotating machine over time. Thus, the device for detecting a malfunction of a rotating machine in the first aspect of the present invention can early detect a malfunction of the rotating machine.

The primary determination of a malfunction of a rotating machine refers to, for example, determination whether the rotating machine has a malfunction and identification of the type of the malfunction, if any (Examples of the type includes contact between rotors or contact between a rotor and a casing enclosing the rotor.) The secondary determination is more computationally intensive than the primary determination (for example, determination of the location of contact between rotors if the rotors are in contact with each other). In the device for detecting a malfunction of a rotating machine in the first aspect of the present invention, the determination unit performs the primary determination but does not perform the secondary determination. Thus, the determination unit can be relatively less computationally intensive. This allows use of a simplified and reduced-size element such as hardware for the determination unit. Thus, the device for detecting a malfunction of a rotating machine in the first aspect of the present invention can have a reduced size, which can make the device portable.

The result of the primary determination may be displayed on the display unit or may be audibly announced.

In the device for detecting a malfunction of a rotating machine, the frequency analyzer preferably analyzes the frequency of the plurality of the sampled data by fast Fourier transform and outputs amplitude data corresponding to the respective frequencies.

In the device for detecting a malfunction of a rotating machine in the preferred implementation, use of fast Fourier transform allows suitable real-time display of the result of the frequency analysis.

In the device for detecting a malfunction of a rotating machine, the display unit displays the result of the frequency analysis in two dimensions: the frequency dimension and the amplitude dimension. More preferably, the display unit displays the result of the frequency analysis at respective times in chronological order, in three dimensions, and in real time.

In the device for detecting a malfunction of a rotating machine in the preferred implementation, the display unit displays the result of the frequency analysis of the sampled data in chronological order, in real time, and in three dimensions: the frequency dimension, the amplitude dimension (the amplitude dimension indicating amplitudes corresponding to respective frequencies), and time dimension, which allows an operator to readily visually recognize a change in operation states of the rotating machine over time.

In the device for detecting a malfunction of a rotating machine, the frequency analyzer initiates the frequency analysis when the frequency analyzer has received the plurality of the sampled data from the detecting unit. Preferably, the period from the initiation of the frequency analysis to the end of the frequency analysis is shorter than the predetermined period described above.

In the device for detecting a malfunction of a rotating machine in the preferred implementation, the frequency analyzer can complete, within the predetermined period, the frequency analysis of all of the plurality of the sampled data received at the beginning of the predetermined period.

In the device for detecting a malfunction of a rotating machine, the storage initiates storage of the plurality of the sampled data and the result of the frequency analysis when the storage has received the plurality of the sampled data from the detecting unit. Preferably, the period from the initiation of storage of the plurality of the sampled data to the end of the storage is shorter than the predetermined period.

In the device for detecting a malfunction of a rotating machine in the preferred implementation, the storage can initiate storage of the plurality of the sampled data and the result of the frequency analysis when the storage has received the data. The device for detecting a malfunction of a rotating machine can store, to the storage within the predetermined period, all of the plurality of the sampled data received at the beginning of the predetermined period.

Preferably, the device for detecting a malfunction of a rotating machine further includes a termination instruction input unit for receiving an instruction to terminate detection of the malfunction. When the termination instruction input unit has received the instruction, the frequency analyzer preferably reads all of the plurality of the sampled data stored in the storage, performs the frequency analysis, and stores the result of the frequency analysis in the storage in chronological order.

In the preferred implementation, the frequency analyzer stores the result of the frequency analysis in chronological order in the storage upon terminating detection of the malfunction, which can reduce the processing load for the storage process, for example via a controller, compared with a case in which the result of the frequency analysis is stored during the frequency analysis.

In the device for detecting a malfunction of a rotating machine, the frequency analyzer is functionally configured with a processor by executing a predetermined frequency-analysis-program. Preferably, the frequency analyzer is functionally configured with the processor upon initiating the frequency analysis, while the frequency analysis is cleared from the processor upon terminating the frequency analysis.

In the device for detecting a malfunction of a rotating machine in the preferred implementation, a plurality of frequency analyzers can be functionally configured in parallel. As the frequency analyzer is configured when necessary, the device for detecting a malfunction of a rotating machine only needs to control the frequency analyzer that is functionally configured with the processor when necessary, which can reduce the processing load of the processor, compared with a case in which a predetermined number of frequency analyzers are functionally pre-configured.

In the device for detecting a malfunction of a rotating machine, the detecting unit preferably includes a sensor for detecting vibration of the rotating machine and outputting a signal indicative of the detected vibration, an attachment part for removably attaching the sensor to the rotating machine, and a sampler for sampling the signal that is indicative of the vibration and is outputted by the sensor with a predetermined sampling frequency and outputting, at a time at intervals of a predetermined period, the plurality of the sampled data detected within the predetermined period.

The attachment part is, for example, a magnet. If the part of the rotating machine where the sensor is attached is nonmagnetic, the attachment part is constituted by, for example, a holder for holding the sensor and a screw for attaching the holder to the rotating machine.

In the preferred implementation, the sensor is removably attached to the rotating machine, and thus the device for detecting a malfunction of a rotating machine is not permanently provided. This is convenient when the device is designed to be intermittently used.

Preferably, the device for detecting a malfunction of a rotating machine further includes a battery receptacle for holding a battery that is a power source for actuating the device.

At a location for inspecting a rotating machine for malfunctions, no electrical outlet may be available as a power source for a device for detecting a malfunction of a rotating machine (for example, in a case in which the rotating machine is installed outside). The device for detecting a malfunction of a rotating machine receives power from a battery and thus can inspect the rotating machine for malfunctions at a location where no electrical outlet is available.

In the device for detecting a malfunction of a rotating machine, the detecting unit preferably includes a sensor for detecting vibration of the rotating machine and outputting a signal indicative of the detected vibration, an attachment part for removably attaching the sensor to the rotating machine, a sampler for sampling the signal that is indicative of the vibration and is outputted by the sensor with a predetermined sampling frequency and outputting, at a time at intervals of a predetermined period, the plurality of the sampled data detected within the predetermined period. And preferably, the device for detecting a malfunction of a rotating machine further includes a battery receptacle for holding a battery that is a power source for actuating the device, a notification unit for providing an optical indication when the determination unit has determined that the rotating machine has a malfunction, an input unit for providing an input for operating the device, and a housing for enclosing the storage, the frequency analyzer, the determination unit, the display unit, the transmitting unit, the sampler, the battery receptacle, the notification unit, and the input unit.

In the preferred implementation, the elements that constitute the device for detecting a malfunction of a rotating machine (the storage, the frequency analyzer, the determination unit, the display unit, the transmitting unit, the sampler, the battery receptacle, the notification unit, and the input unit) are enclosed in a single housing, which can make the device portable.

The second aspect of the present invention is a system for detecting a malfunction of a rotating machine, the system including a device for detecting a malfunction of a rotating machine, the device including a detecting unit for sampling and detecting vibration of the rotating machine with a predetermined sampling frequency, and outputting, at a time at intervals of a predetermined period, a plurality of the sampled data detected within the predetermined period, a storage for storing the plurality of the sampled data outputted by the detecting unit, a frequency analyzer for analyzing the frequency of the plurality of the sampled data outputted by the detecting unit, a determination unit for performing a primary determination based on the result of the frequency analysis by the frequency analyzer, a display unit for displaying the result of the frequency analysis by the frequency analyzer in chronological order and in real time, and a transmitting unit for transmitting the plurality of the sampled data outputted by the detecting unit, and an information-processing device that includes a receiver for receiving the plurality of the sampled data transmitted by the transmitting unit, a second frequency analyzer for analyzing the frequency of the plurality of the sampled data received by the receiver, and a second determination unit for performing a secondary determination based on the result of the frequency analysis by the second frequency analyzer.

The second aspect of the present invention has the same effects as the first aspect of the present invention.

Effects of the Invention

The present invention allows early detection of a malfunction of a rotating machine. The present invention also allows reduction in size of a device for detecting a malfunction of a rotating machine, which can provide a portable device for detecting a malfunction of a rotating machine.

BRIEF DESCRIPTION OF THE DRAWINGS

FIGS. 4A, 4B and 4C are flowcharts illustrating the operations of a device for detecting a malfunction of a rotating machine according to an embodiment of the present invention.

DESCRIPTION OF THE EMBODIMENTS

Figure 1:
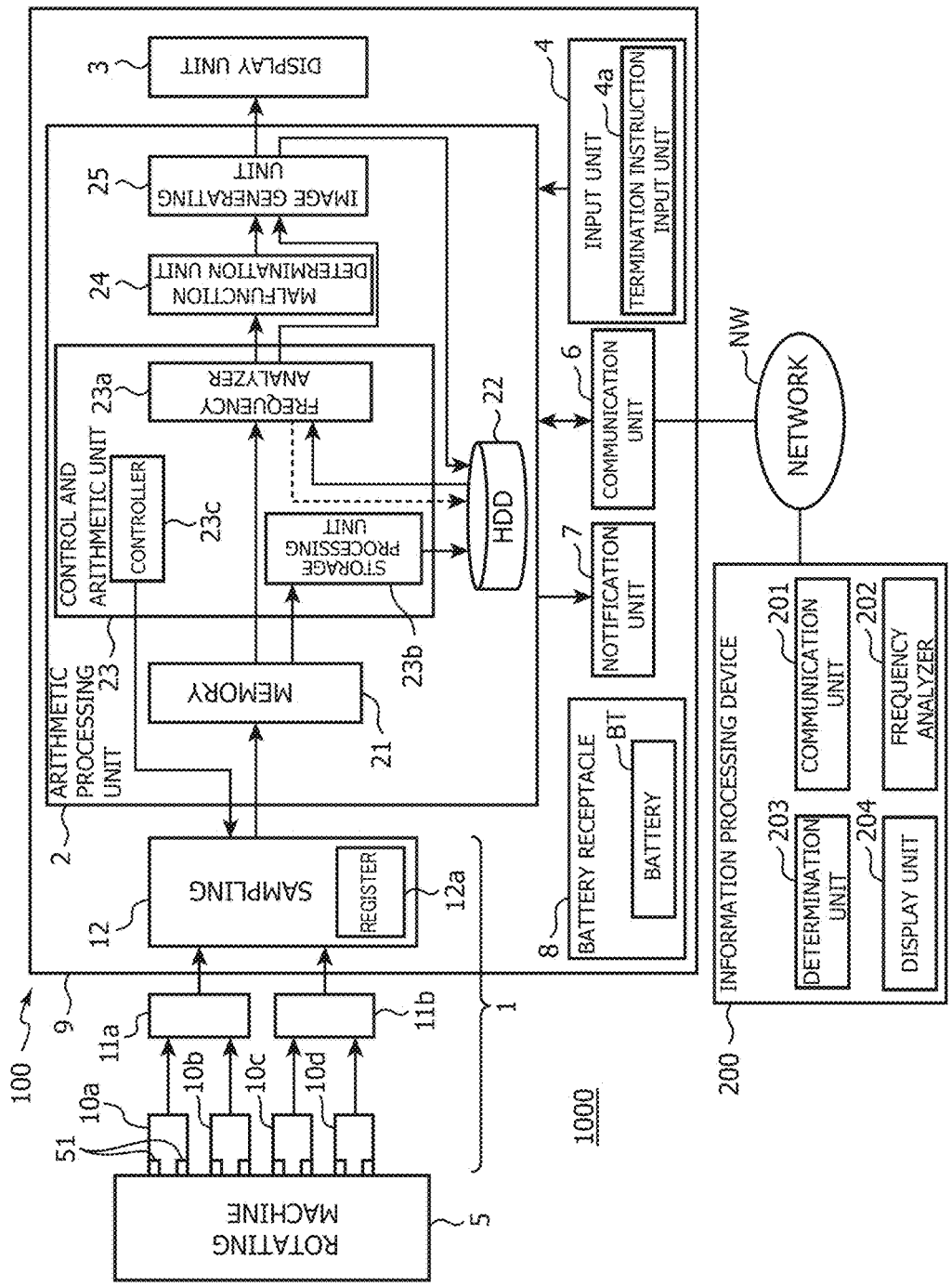
FIG. 1 is a block diagram illustrating an exemplary configuration of a system for detecting a malfunction of a rotating machine according to an embodiment of the present invention.

Now, an embodiment of the present invention will be described with reference to the drawings. In the drawings, like references designate like elements, the description of which is omitted if unnecessary. As used herein, a numeral with no letter suffix indicates a generic element, while a numeral with a letter suffix indicates an individual element.

FIG. 1 is a block diagram illustrating an exemplary configuration of a system 1000 for detecting a malfunction of a rotating machine (hereinafter also simply referred to as "system for detecting a malfunction") according to an embodiment. As illustrated in FIG. 1, the system 1000 for detecting a malfunction includes a device 100 for detecting a malfunction of a rotating machine and an information-processing device 200. The device 100 for detecting a malfunction of a rotating machine and the information-processing device 200 are communicatively connected to each other via network NW. Examples of the network NW include the Internet and LAN (local area network). The device 100 for detecting a malfunction of a rotating machine includes, for example, a detecting unit 1, an arithmetic processing unit 2, a display unit 3, an input unit 4, a communication unit 6, a notification unit 7, a battery receptacle 8, and a housing 9. The arithmetic processing unit 2 is connected to the detecting unit 1, the display unit 3, the input unit 4, the communication unit 6, and the notification unit 7.

The detecting unit 1 detects vibration of a rotating machine 5 to be inspected; samples and detects the vibration with a predetermined sampling frequency, and outputs, to the arithmetic processing unit 2 at a time at intervals of a predetermined period, all of a plurality of the sampled data detected within the predetermined period. The detecting unit 1 includes, for example, sensors 10 (10a-10d), amplifiers 11 (11a and 11b) and a sampler 12. The sensors 10 are connected to the amplifiers 11, which are connected to the sampler 12. The sampler 12 is connected to the arithmetic processing unit 2.

The sensors 10 detect vibration of the rotating machine 5 to be inspected and output a signal indicative of the detected vibration. For example, the sensors 10 are an electro-mechanical energy converting element that contains a material such as piezoceramics and converts vibrational mechanical energy to electrical energy. More particularly, the sensors 10 are, for example, AE (acoustic emission) sensors, acceleration sensors, or the like. One or more sensors 10 may be used. In the embodiment, two AE sensors 10a and 10b and two acceleration sensors 10c and 10d are used. As illustrated in FIG. 1, the AE sensors 10a and 10b and the acceleration sensors 10c and 10d are attached to the body of the rotating machine 5 such as a turbine and a compressor. For example, when the rotating machine 5 is a compressor, the AE sensors 10a and 10b detect a malfunction of rotors or the like, such as contact of two rotors that are usually spaced from each other, by detecting AE waves due to the malfunction. The acceleration sensors 10c and 10d detect the vibration acceleration of the rotating machine 5 due to the malfunction.

The sensors 10 include magnets 51. The sensors 10 have a surface in contact with the rotating machine 5, and a part of the surface is composed of the magnets 51. The magnets 51 are an example of the attachment part and removably attach the sensors 10 to the rotating machine 5. The attachment part is not limited to magnets and may be constituted by, for example, a holder for holding the sensors 10 and a screw for attaching the holder to the rotating machine 5. Such configuration allows attachment of the sensors 10 to the rotating machine 5 even if the parts of the rotating machine 5 where the sensors 10 are attached are nonmagnetic.

The sensors 10 are removably attached to the rotating machine 5 by the magnets 51, and thus the device 100 for detecting a malfunction of a rotating machine is not permanently connected to the machine 5. This is convenient when the device is designed to be intermittently used.

The amplifiers 11 amplify each small detected signal outputted by the sensors 10. The number of the amplifiers 11 depends on the number of the sensors 10. In the embodiment, two amplifiers 11*a* and 11*b* are used. The amplifier 11*a* is connected to the AE sensors 10*a* and 10*b*. The amplifier 11*b* is connected to the acceleration sensors 10*c* and 10*d*. The amplifier 11*a* individually amplifies each signal outputted by the AE sensors 10*a* and 10*b* and individually outputs each amplified signal. The amplifier 11*b* individually amplifies each signal outputted by the acceleration sensors 10*c* and 10*d* and individually outputs each amplified signal. The each of the signals amplified by the amplifiers 11*a* and 11*b* is outputted to the sampler 12.

The sampler 12 samples the vibration of the rotating machine 5 with a predetermined sampling frequency and outputs all of the plurality of the sampled data to the arithmetic processing unit 2. All of the plurality of the sampled data are outputted at a time by the sampler 12 as instructed by the arithmetic processing unit 2. For example, in the embodiment, the sampler 12, which includes, for example, a register 12*a*, individually samples each signal that is, for example, detected by the AE sensors 10*a* and 10*b* and that is individually outputted by the amplifier 11*a* with a sampling frequency of 1 MHz at the same timing; A/D-converts the signal; and stores the signal in the register 12*a*. On the other hand, the sampler samples each signal that is detected by the acceleration sensors 10*c* and 10*d* and individually outputted by the amplifier 11*b* with a sampling frequency of 20 kHz at the same timing; A/D converts the signal; and stores the signal in the register 12*a*. Therefore, all of the sampled data Da are stored in the register 12*a*. The sampler 12 outputs, to the arithmetic processing unit 2 at a time at intervals of a predetermined period, all of the sampled data Da that are detected within the predetermined period and that are stored in the register 12*a*, as instructed by the arithmetic processing unit 2. The register 12*a* assembles the signals detected by the AE sensors 10*a* and 10*b*, amplified by the amplifier 11*a*, sampled, and A/D converted (hereinafter also referred to as "AE data") into a single electronic file with the arrival of every predetermined number of the signals, for example every 102,400 signals, and outputs the signals at a time to the arithmetic processing unit 2. The AE data is outputted to the arithmetic processing unit 2 at intervals of about 0.1 sec (102,400/1 MHz≈about 0.1 sec). For the AE data, the predetermined period is about 0.1 sec in the embodiment. The register 12*a* also assembles the signals outputted by the acceleration sensors 10*c* and 10*d*, amplified by the amplifier 11*b*, sampled, and A/D converted (hereinafter also referred to as "acceleration data") into a single electronic file with the arrival of every predetermined number of signals, for example, every 65,536 signals and outputs the signals at a time to the arithmetic processing unit 2. The acceleration data is outputted to the arithmetic processing unit 2 at intervals of about 3.3 sec (65,536/20 kHz≈about 3.3 sec). For the acceleration data, the predetermined period is about 3.3 sec in the embodiment.

In the detecting unit 1, each sensor 10 detects vibration of the rotating machine 5 and outputs an analog signal indicative of the vibration to its corresponding amplifier 11. Then, the amplifier 11 amplifies the signal, which is then inputted to the sampler 12. The sampler 12 samples and digitizes the inputted signal before outputting the signal to the arithmetic processing unit 2 at a predetermined timing.

As described above, the sampler 12 samples signals that are indicative of the vibration and are outputted by the sensors 10 with a predetermined sampling frequency and outputs, at a time at intervals of a predetermined period, all of the plurality of the sampled data detected within the predetermined period. Instead of outputting all of the plurality of the sampled data at a time, the sampler 12 may output part of the plurality of the sampled data at a time. More particularly, instead of outputting, for example, 102,400 sampled signals at a time, the sampler 12 may output part of 102,400 sampled signals (for example, 51,200 sampled signals) at a time.

The arithmetic processing unit 2 analyzes the frequency of the sampled data Da detected by the detecting unit 1 and generates an image data for displaying, in chronological order and in real time, the result of the frequency analysis of the signals detected within the predetermined period. The arithmetic processing unit 2 includes, for example, a memory 21, a HDD (hard disk drive) 22, a control and arithmetic unit 23, a malfunction determination unit 24, and an image generating unit 25. The memory 21 and the HDD 22 are examples of the storage for storing the sampled data Da outputted by the detecting unit 1. The sampler 12 is connected to each of the memory 21 and the control and arithmetic unit 23. The memory 21 is connected to the control and arithmetic unit 23. The control and arithmetic unit 23 is connected to each of the HDD 22, the malfunction determination unit 24, and the image generating unit 25. The malfunction determination unit 24 is connected to the image generating unit 25. The image generating unit 25 is connected to each of the display unit 3 and the HDD 22. The control and arithmetic unit 23 provides an output to the malfunction determination unit 24 and the image generating unit 25. In particular, the control and arithmetic unit 23 provides an output via the malfunction determination unit 24 to the image generating unit 25. The image generating unit 25 provides an output to the display unit 3. The HDD 22 receives an image data from the image generating unit 25.

The memory 21 temporarily stores all of the sampled data Da outputted by the sampler 12. The control and arithmetic unit 23 reads the sampled data Da stored in the memory 21. The memory 21 allows all of the sampled data Da outputted at a time by the sampler 12 to be held. Then, all of the sampled data Da can be stored on the HDD 22, and a frequency analyzer 23*a* can use all of the sampled data Da to analyze the frequency.

The HDD 22 stores the sampled data Da outputted by the detecting unit 1. In the embodiment, for example, a storage processing unit 23*b*, which is described below, stores, on the HDD 22, all of the sampled data Da stored in the memory 21. In the embodiment, the storage processing unit 23*b* initiates storage of the sampled data Da on the HDD 22 when, for example, the unit 23*b* has received the sampled data Da from the detecting unit 1.

The control and arithmetic unit 23 provides overall control of the detecting unit 1, the arithmetic processing unit 2, the display unit 3, the input unit 4, the communication unit 6, and the notification unit 7 and performs various arithmetical operations. The control and arithmetic unit 23 includes, for example, a processor such as a CPU (central processing unit), a ROM (read only memory), a RAM (random access memory) with the memory 21 functionally configured therewith, and their peripheral circuits. The control and arithmetic unit 23 includes, for example, the frequency analyzer 23*a*, the storage processing unit 23*b*, and a controller 23*c*. In the embodiment, the control and arithmetic unit 23 executes a malfunction detection program for detecting a malfunction, the program being stored in the ROM, so that the frequency analyzer 23a, the storage processing unit 23b, and the controller 23c are functionally configured in the control and arithmetic unit 23. In the control and arithmetic unit 23, a plurality of the frequency analyzers 23a can be functionally configured in parallel so that the plurality of the frequency analyzers 23a can be executed in parallel. In the embodiment, upon initiating the frequency analysis, the frequency analyzer 23a and the storage processing unit 23b are functionally configured in the control and arithmetic unit 23, for example, simultaneously, while upon completing the frequency analysis, the frequency analyzer 23a and the storage processing unit 23b are cleared from the control and arithmetic unit 23. The frequency analyzer 23a is connected to the memory 21 and the HDD 22 and provides an output to the malfunction determination unit 24 and the image generating unit 25. The storage processing unit 23b is connected to the memory 21 and the HDD 22.

The frequency analyzer 23a analyzes the frequency of the sampled data Da outputted from the sampler 12. In the embodiment, for example, the frequency analyzer 23a analyzes the frequency of the sampled data Da by fast Fourier transform (FFT) and output frequency characteristics of the sampled data Da, i.e., amplitude values corresponding to the respective frequencies.

The frequency analyzer 23a performs fast Fourier transform of the AE data, for example, every 4096 signals. As described above, the AE data is inputted to the memory 21 at a time, every 102,400 signals, and thus fast Fourier transform of the AE data is performed 25 times (102400/4096=25) within the predetermined period (about 0.1 sec). The frequency analyzer 23a uses, for example, the average values of the results of 25 times fast Fourier transform obtained within the predetermined period as the result of the fast Fourier transform in the predetermined period. The fast Fourier transform of the acceleration data is performed, for example, every 65,536 signals. As described above, the acceleration data is inputted to the memory 21 at a time, every 65,536 signals, and thus the fast Fourier transform of the acceleration data is performed once within the predetermined period (about 3.3 sec). When the termination instruction input unit (input unit) 4 has received an instruction to terminate detection of malfunctions from an operator who operates the device 100 for detecting a malfunction, the frequency analyzer 23a reads the sampled data Da at all of the times from the HDD to analyze the frequency of the data and then outputs the results of the frequency analysis to the image generating unit 25.

The storage processing unit 23b stores, on the HDD 22, the sampled data Da read from the memory 21. The controller 23c provides overall control or the like of the arithmetic processing unit 2. The controller 23c outputs an instruction to the sampler 12 to output all of the sampled data Da at a time. In the embodiment, the instruction to output the data at a time is outputted by the controller 23c to the sampler 12 at intervals of the predetermined period. The controller 23c outputs an instruction to the sampler 12 to start sampling and A/D conversion.

The malfunction determination unit 24 uses the result of the frequency analysis by the frequency analyzer 23a to determine the presence of a malfunction of, for example, rotors of the rotating machine 5 (primary determination). The malfunction determination unit 24 extracts characteristic values such as, for example, the maximum value, average, or standard deviation of the amplitudes or the median or standard deviation of the frequencies from the result of the frequency analysis and determines whether the characteristic values meet a predetermined criterion by comparing the characteristic values with a predetermined threshold based on, for example, a past malfunction data, an experimental result, or a simulation result to determine the presence of a malfunction of, for example, the rotors. When the rotating machine 5 is a compressor, the malfunction determination unit 24 outputs, to the image generating unit 25, an alarm message, for example, that indicates suspected contact between the two rotors as the result of the malfunction determination.

In this manner, the malfunction determination unit 24 functions to perform a primary determination of a malfunction of the rotating machine 5 based on the result of the frequency analysis by the frequency analyzer 23a. The primary determination is, for example, to determines whether the rotating machine 5 has a malfunction and to determine what types of malfunctions the rotating machine 5 has (for example, contact between rotors or contact between a rotor and a casing enclosing the rotor) if the rotating machine 5 has a malfunction.

Figure 2:
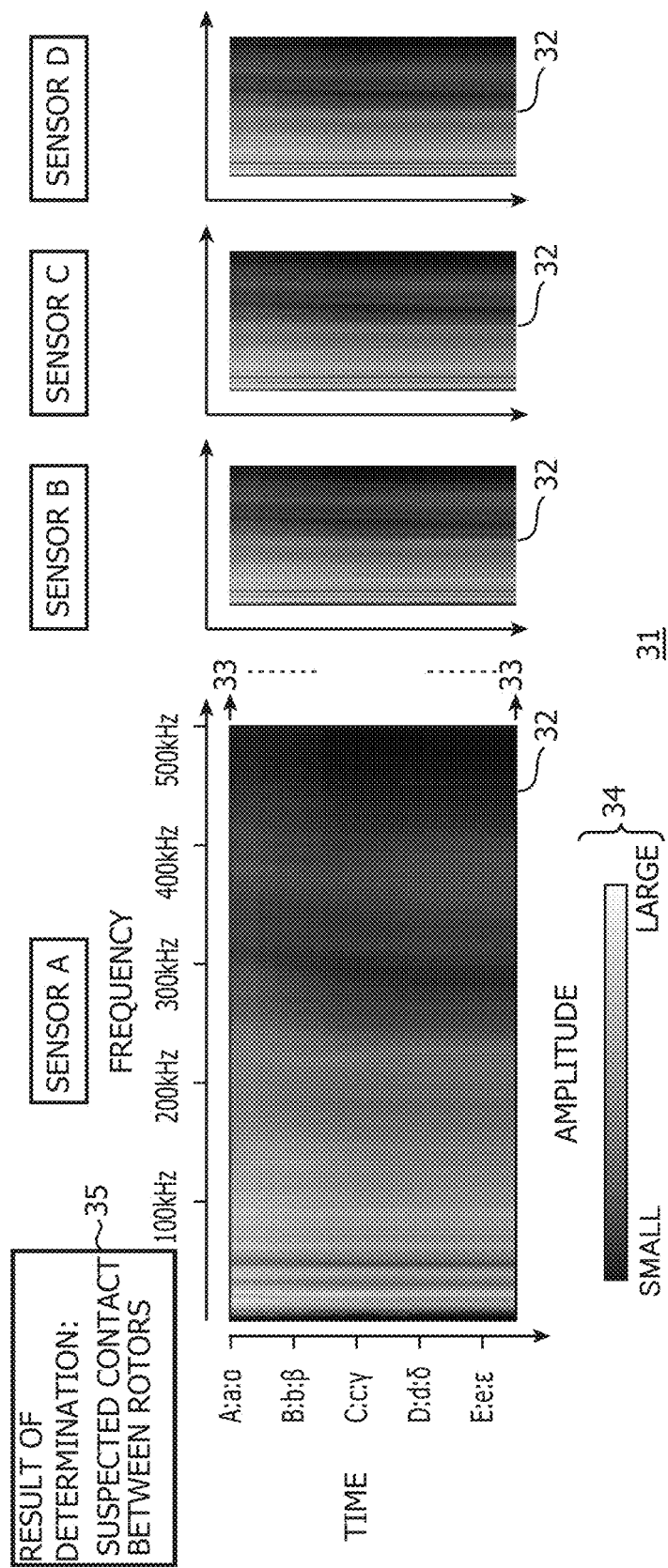
FIG. 2 is an exemplary image displayed on a display unit according to an embodiment of the present invention.

The image generating unit 25 generates an image data to be displayed on the display unit 3. The image generating unit 25 generates, for example, an image data showing the result of the frequency analysis in chronological order and in real time. The image data shows the result of the frequency analysis in, for example, two dimensions: the frequency dimension and the amplitude dimension. The image data also shows the two dimensional result (the result of the frequency analysis) at the most current time point and previous time points in chronological order, thereby displaying the data in real time and in three dimensions (hereinafter such data is also referred to as "three-dimensional image data"). FIG. 2 illustrates an exemplary image displayed on a display screen 31 of the display unit 3. The display screen 31 displays partial images 32 (images of the three-dimensional image data) from each of the sensors (Sensor A, Sensor B, Sensor C, and Sensor D in FIG. 2 respectively correspond to the AE sensor 10a, the AE sensor 10b, the acceleration sensor 10c, and the acceleration sensor 10d), the display screen 31 showing the result of the frequency analysis at most current time point (E:e:ε in FIG. 2) and the result of the frequency analysis at previous time points (from A:a:α to E:e:ε in FIG. 2) in chronological order, in three dimensions, and in real time. The display screen 31 also has a result-displaying portion 35 on which the result of the determination (such as an alarm message) is displayed at a predetermined location, and a legend image 34, which is described below. The partial images 32 show the result of the frequency analysis, where time is taken along the ordinate, and frequency is taken along the abscissa. For convenience of description, the image of Sensor A is larger than the images of Sensors B-D in FIG. 2. The partial images 32 of the respective sensors are a planar image that is constituted by, for example, band partial images 33 arranged side by side in chronological order and that shows data in two dimensions: the frequency dimension and the amplitude dimension. In FIG. 2, the oldest amplitude data (a two-dimensional band partial image 33) is deleted from the partial images 32, and the partial images 33 at the remaining time points are scrolled by the length for the deleted data. The latest partial image 33 at the most current time point is added at the bottom of the partial image 32.

In the embodiment, the amplitude data corresponding to the respective frequencies are shown, for example, using white and various shades of gray. The partial images 33 are, for example, constituted by a plurality of pixels of white or various shades of gray in the frequency dimension depending on the amplitude levels and are displayed as a band of white and various shades of gray in two dimensions. In FIG. 2, the relationship between the amplitude data and the shades is illustrated by a legend image 34 displayed on a predetermined location on the display screen 31.

The band partial images 33 displayed in the two dimensions are constituted by, for example, 2,048 pixels arranged in the direction of the frequency dimension. In particular, the partial images 33 represent amplitude values for 2,048 frequencies. If the frequency analyzer 23a outputs the result of frequency analysis of more than 2,048 frequencies, 2,048 frequencies are selected from the outputted frequencies in a predetermined extraction operation to generate a partial image 33. For example, if the result of frequency analysis of 4,096 frequencies is outputted, 2,048 frequencies are selected by comparing amplitude values of two adjacent frequencies and selecting the frequency that has a higher amplitude value so as to generate a band partial image 33 constituted by 2,048 pixels arranged in the direction of the frequency dimension. As described above, selection of frequencies having a higher amplitude value, i.e., indicating a more severe malfunction allows the device 100 for detecting a malfunction to more suitably detect a malfunction.

If the termination instruction input unit (input unit) 4 has received an instruction to terminate detection of malfunctions from an operator, the image generating unit 25 receives the results of analysis of frequencies (the amplitude data) at all of the time points from the frequency analyzer 23a and then generates a three-dimensional image data that shows the results of analysis of frequencies at all of the time points, as described above. Then the three-dimensional image data is transferred to and stored on the HDD 22.

The display unit 3 receives the image data from the image generating unit 25 and displays the result of the frequency analysis by the frequency analyzer 23a in chronological order and in real time.

The display unit 3 displays the result of the primary determination. For example, if the malfunction determination unit 24 has determined that the rotating machine 5 has a malfunction, the display unit 3 displays an indication of the malfunction (for example, an alarm message). The indication of the malfunction is displayed on, for example, the result-displaying portion 35 in FIG. 2. The result of the primary determination may be audibly announced.

In inspection of the rotating machine 5 for malfunctions, not all of the four sensors 10 may be used, and fewer than four sensors 10 may be used. For example, only the AE sensor 10a may be used. In this case, the remaining three sensors 10 do not send any signals to the sampler 12 and the arithmetic processing unit 2, and thus the arithmetic processing unit 2 cannot generate four partial images 32. This could interfere with normal operations of the arithmetic processing unit 2. To prevent this, a sensor signal input unit (not shown) is disposed before the sampler 12. A user can operate the input unit 4 to select a sensor 10 to be used for detecting a malfunction of the rotating machine 5 from the four sensors 10. For example, if only the AE sensor 10a is selected, the sensor signal input unit activates signals from the AE sensor 10a and invalidates signals from the remaining sensors 10. The sampler 12 generates a plurality of the sampled data for the signals from the AE sensor 10a, and the arithmetic processing unit 2 uses the data to analyze the frequency and then generates a partial image 32 for Sensor A.

The input unit 4 is an input device such as a mouse or keyboard for inputting information to the arithmetic processing unit 2. The input unit 4 provides an input for operating the device 100 for detecting a malfunction of a rotating machine. The input unit 4 includes a termination instruction input unit 4a that receives an instruction to terminate detection of malfunctions from an operator. The termination instruction input unit 4a may, for example, be a predetermined key on the keyboard or a predetermined field on the display unit 3 for receiving a termination instruction input (a termination instruction input button).

The communication unit 6 is a communication interface circuit that performs communication with the information-processing device 200 connected to the network NW. As described above, the detecting unit 1 samples and detects vibration of the rotating machine 5 with a predetermined sampling frequency and outputs, at a time at intervals of a predetermined period, a plurality of the sampled data detected within the predetermined period. The communication unit 6, which functions as a transmitting unit, transmits the plurality of the sampled data outputted by the detecting unit 1 to the information-processing device 200 for performing a secondary determination.

When the malfunction determination unit 24 (an exemplary determination unit) has determined that the rotating machine 5 has a malfunction, the notification unit 7 provides an optical indication. For example, a very small rotating light is used as the notification unit 7. A user such as an operator of the rotating machine 5 may use a stethoscope in combination with the device 100 for detecting a malfunction of a rotating machine to inspect the rotating machine 5 for malfunctions. In this case, it is contemplated that the user uses a stethoscope at a location remote from the device 100 for detecting a malfunction of a rotating machine to inspect the rotating machine 5 for malfunctions. During operation of the rotating machine 5, the rotating machine 5 generates noises, and thus the user may not recognize an audio indication (e.g., beep) of detection of a malfunction when the device 100 detects the malfunction. Thus, the notification unit 7 provides an optical indication of detection of a malfunction.

The battery receptacle 8, which is referred to as battery holder, battery box, or battery case, holds a battery BT that is a power source for actuating the device 100 for detecting a malfunction of a rotating machine. The battery BT provides the power necessary to operate the arithmetic processing unit 2, the display unit 3, the input unit 4, the communication unit 6, the notification unit 7, and the sampler 12.

At a location for inspecting the rotating machine 5 for malfunctions, no electrical outlet as a power source may be available for the device 100 for detecting a malfunction of a rotating machine (for example, in a case in which the rotating machine 5 is installed outside). In the embodiment, the device 100 for detecting a malfunction of a rotating machine receives power from the battery BT and thus can inspect the rotating machine 5 for malfunctions at a location where no electrical outlet is available.

The housing 9 encloses the arithmetic processing unit 2, the display unit 3, the input unit 4, the communication unit 6, the notification unit 7, the battery receptacle 8, and the sampler 12. In the embodiment, the elements that constitute the device 100 for detecting a malfunction of a rotating machine (the arithmetic processing unit 2, the display unit 3, the input unit 4, the communication unit 6, the notification unit 7, the battery receptacle 8, and the sampler 12) are enclosed in the single housing. Thus, in the embodiment, the device 100 for detecting a malfunction of a rotating machine can be a mobile terminal (for example, a laptop computer or a tablet), which can provide a portable device for detecting a malfunction of a rotating machine.

The information-processing device 200 will be described later.

Figure 3:
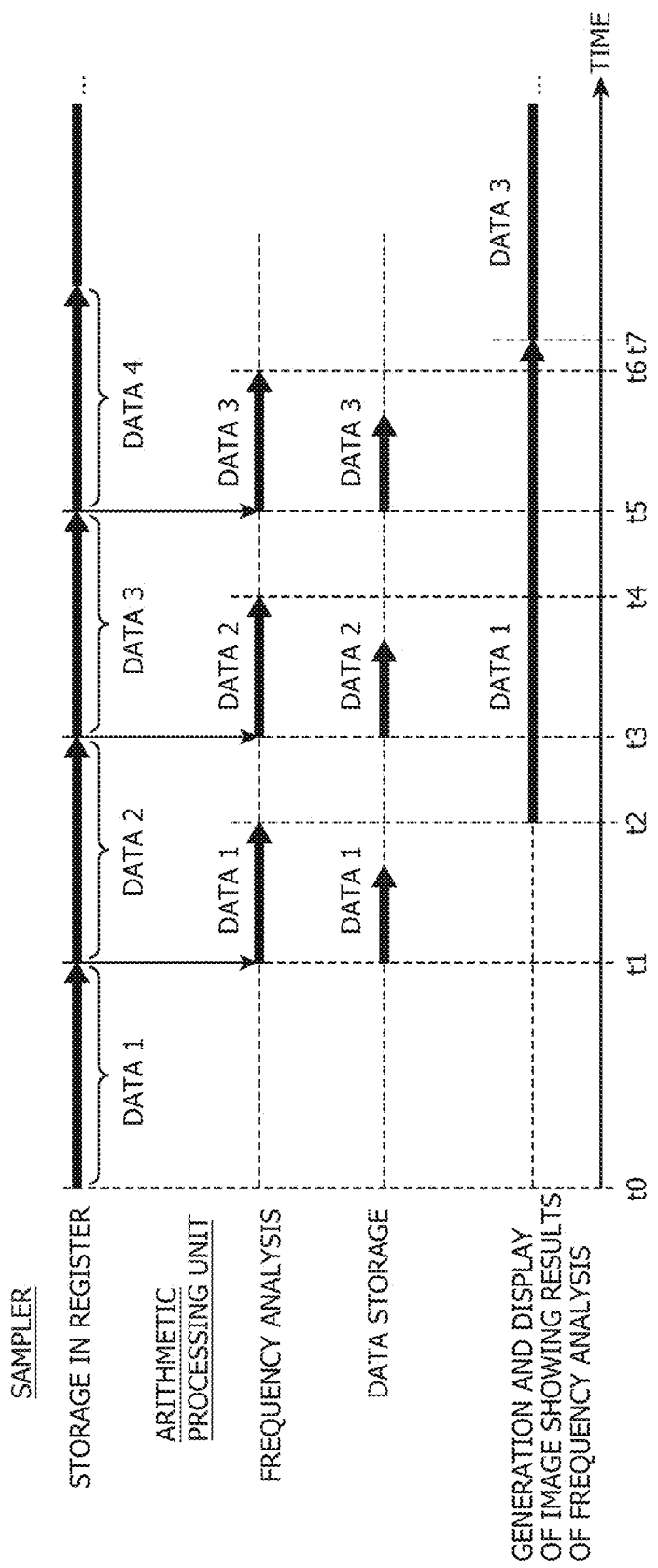
FIG. 3 is a timing chart illustrating the operation of a device for detecting a malfunction of a rotating machine according to an embodiment of the present invention.

FIG. 3 is a timing chart illustrating the operation of the device 100 for detecting a malfunction of a rotating machine according to the embodiment. FIG. 3 illustrates a timing chart of data in the device 100 for detecting a malfunction. The timing charts of storage processing in the register 12a ("Storage in Register" in FIG. 3), frequency analysis by the frequency analyzer 23a ("Frequency Analysis" in FIG. 3), storage processing in the storage processing unit 23b ("Data Storage" in FIG. 3), and image generation processing by the image generating unit 25 and image display processing by the display unit 3 ("Generation and Display of Image Showing Results of Frequency Analysis" in FIG. 3) are taken along the ordinate. Time is taken along the abscissa. The data are stored in the register 12a at intervals of a predetermined period. Time t0 is the time at which the controller 23c instructs the sampler 12 to initiate sampling and A/D conversion. In the period from Time t0 to Time t1, at which the predetermined period has elapsed from Time t0, the sensors 10 (the AE sensors 10a and 10b and the acceleration sensors 10c and 10d) detect vibration of the rotating machine 5, the amplifiers 11 (11a and 11b) amplify the signals, the sampler 12 samples and A/D coverts the signals, and the register 12a stores the sampled data Da (Data 1 in FIG. 3). At Time t1, all of the plurality of the sampled data Da (Data 1) detected within the predetermined period are stored in the register 12a, and then the sampled data Da (Data 1) stored are outputted by the register 12a to the memory 21 at a time, as instructed by the controller 23c. Similarly, in the period from Time t1 to Time t3, at which the predetermined period has elapsed, the detecting unit 1 detects the vibration, samples and A/D converts the signals, and stores the sampled data Da (Data 2 in FIG. 3) in the register 12a again. At Time t3, all of the sampled data Da (Data 2) detected within the predetermined period are stored in the register 12a, and then are outputted by the register 12a to the memory 21 at a time, as instructed by the controller 23c. In this manner, all of the plurality of the sampled data Da detected within the predetermined period are stored in the register 12a at intervals of the predetermined period, and all of the plurality of the sampled data Da are outputted at a time. Also after Time t3, data such as Data 3 are stored in the register 12a and outputted to the memory 21 in the same manner.

After Time t1, all of the sampled data Da (Data 1) outputted by the register 12a at a time are temporarily stored in the memory 21. When the frequency analyzer 23a has received the sampled data Da from the register 12a via the memory 21 (at Time t1), the frequency analyzer 23a initiates analysis of the frequency of the sampled data Da (Data 1). When the storage (the HDD 22 in the embodiment) has received the sampled data Da from the register 12a via the memory 21 and the storage processing unit 23b (at Time t1), the storage initiates storage of Data 1. In the embodiment, the frequency analysis and storage of the plurality of the sampled data Da in the storage are completed by Time t2, which is before Time t3. In other words, the analysis period from initiation of analysis of the frequency of the sampled data Da (Data 1) to completion of the analysis (from Time t1 to Time t2) is shorter than the predetermined period (from Time t1 to Time t3). The storage period from initiation of the storage of the sampled data Da (Data 1) to completion of the storage is also shorter than the predetermined period (from Time t1 to Time t3). The arithmetic processing unit 2 is a hardware device that can achieve such operations. The analysis period and the storage period that are shorter than the predetermined period allow frequency analysis of all of the sampled data Da outputted from the sampler 12 at a time and allow storage of all of the sampled data Da in the storage. At time points after Time t1, such as Time t3, Time t5, and so on, the frequency analyzer 23a analyzes the frequency of all of the sampled data Da (such as Data 2, Data 3, and so on) at intervals of the predetermined period, while the storage processing unit 23b stores all of the sampled data Da (such as Data 2, Data 3, and so on) on the HDD 22. The analysis period and the storage period for data such as Data 2, Data 3, and so on are also shorter than the predetermined period.

After the frequency analyzer 23a completes analysis of the frequency of all of the sampled data Da (Data 1) at Time t2, the result of the frequency analysis is outputted from the frequency analyzer 23a to the malfunction determination unit 24 and the image generating unit 25. Then, the malfunction determination unit 24 initiates the malfunction determination, and the image generating unit 25 produces partial images 33 showing the result of the analysis of the frequency of Data 1 for the respective sensors. The image generating unit 25 generates a partial image 32 (three-dimensional data image) showing the data in chronological order and in real time and an image for a display screen 31 and outputs the images onto the display unit 3. When the result of the malfunction determination by the malfunction determination unit 24 is inputted to the image generating unit 25, the image generating unit 25 also uses the result of the malfunction determination to generate the image data for the display screen 31. Then, the display unit 3 displays the display screen 31. In the embodiment, the period required for the image generating unit 25 to generate the image data for the display screen 31 is longer than the predetermined period, and thus during generation of the image data for the display screen 31, a plurality of the frequency analysis processes may be completed, and a plurality of results of the frequency analysis processes may be provided. In this case, in the embodiment, the image generating unit 25 uses only the most current frequency analysis processes to generate the image data for the display screen 31. For example, in FIG. 3, generation of the image data for the display screen 31 by using the result of the frequency analysis of Data 1 is completed at Time t7, which is later than Time t4, at which the frequency analysis of Data 2 is completed and Time t6, at which the frequency analysis of Data 3 is completed. Thus, the data at Time t7 contains the result of the frequency analysis of Data 2 and the result of the frequency analysis of Data 3. In this case, the image generating unit 25 uses only the image data (partial images 33) for the result of the frequency analysis of Data 3, which is the most current result, to generate the image data for the display screen 31. Thus, at Time t7, the image generating unit 25 does not use the result of the frequency analysis of Data 2 but instead, uses the result for Data 3 to initiate generation of the image data for the display screen 31. Then, the display unit 3 displays the display screen 31. After Time t7, the malfunction determination unit 24 performs a malfunction determination, the image generating unit 25 generates image data for the display screen 31, and the display unit 3 displays the display screen 31 in the same manner.

FIGS. 4A, 4B and 4C are flowcharts illustrating the operations of the device 100 for detecting a malfunction of a rotating machine according to the embodiment. FIG. 4A illustrates an operation flow of the sampler 12. FIG. 4B illustrates an operation flow of the frequency analyzer 23a, the storage processing unit 23b, and the malfunction determination unit 24. FIG. 4C illustrates an operation flow of the image generating unit 25 and the display unit 3. The operations illustrated in FIGS. 4A-4C are performed in parallel.

In FIG. 4A, the arithmetic processing unit 2 (the controller 23c) outputs an instruction to the sampler 12 to start sampling and A/D conversion of outputs from the amplifiers 11. The sensors 10 detect vibration of the rotating machine 5, the amplifiers 11 amplify a signal indicative of the vibration, and the sampler 12 samples and A/D converts the signal and stores the sampled data Da in the register 12a (Step S11). From this point, the number of the sampled and A/D converted data Da stored in the register 12a (hereinafter also referred to as "number of the A/D converted data received") begins increasing from zero. Then, the controller 23c determines whether the number of the A/D converted data received reaches the predetermined number as described above (102,400 signals for the AE data and 65,536 signals for the acceleration data) (Step S13). If the number of data stored is smaller than the predetermined number (NO in Step S13), the determination in Step S13 is performed again, during which the sampled data Da are stored in the register 12a to increase the number of the A/D converted data received. If the number of data stored reaches the predetermined number (YES in Step S13), all of the sampled data Da sent from the register 12a to the arithmetic processing unit 2 (the memory 21) within the predetermined period (at intervals of the predetermined period) are outputted at a time (Step S15). Then, the number of the A/D converted data received is reset (Step S17), and the controller 23c determines whether the input unit (termination instruction input unit) 4 has received an instruction to terminate detection of malfunctions from an operator (Step S19). If the input unit 4 does not receive an instruction to terminate detection of malfunctions from an operator (NO in Step S19), the operation flow goes back to Step S13 to repeat the operations such as the operation of outputting, at a time at intervals of a predetermined period, all of the plurality of the sampled data Da sent within the predetermined period in Step S15. If the input unit 4 has received an instruction to terminate detection of malfunctions from an operator (YES in Step S19), the device 100 for detecting a malfunction performs a predetermined near-final process and then terminates detection of malfunctions.

In FIG. 4B, the controller 23c determines whether all of the sampled data Da sent from the register 12a within the predetermined period, the data being for frequency analysis, are stored in the memory 21 (Step S21). If the controller 23c has determined that the data are not stored (NO in Step S21), the operation flow goes back to Step S21. If the controller 23c has determined that the data are stored (YES in Step S21), the frequency analyzer 23a analyzes the frequency of all of the sampled data Da sent within the predetermined period at intervals of the predetermined period (for example, sufficient time intervals such as 1 sec to ascertain the tendency (trend) of the result of the frequency analysis) (Step S23a). In parallel, the storage processing unit 23b stores, on the HDD 22, all of the sampled data Da sent within the predetermined period (Step S23b). After the frequency analyzer 23a performs the frequency analysis, the malfunction determination unit 24 uses the result of the frequency analysis to determine presence of a malfunction of the rotating machine 5 such as a rotor (Step S25). Then, the controller 23c determines whether the input unit (termination instruction input unit) 4 has received an instruction to terminate detection of malfunctions from an operator (Step S27). If the input unit 4 does not receive an instruction to terminate detection of malfunctions from an operator (NO in Step S27), the operation flow goes back to Step S21. If the input unit 4 has received an instruction to terminate detection of malfunctions from an operator (YES in Step S27), the device 100 for detecting a malfunction performs a predetermined near-final process and then terminates detection of malfunctions. In the predetermined near-final process, the frequency analyzer 23a reads the sampled data Da at all of the times from the HDD 22 to perform frequency analysis and outputs the result of the frequency analysis to the image generating unit 25 (Step S29).

In FIG. 4C, first, the image generating unit 25 determines whether the result of the frequency analysis is inputted (Step S31). If the data of the result of frequency analysis is not inputted (NO in Step S31), the operation flow goes back to Step S31. If the data of the result of the frequency analysis is inputted (YES in Step S31), the image data for the display screen 31 is generated (Step S33), and the image data is outputted to the display unit 3, which displays the image data (Step S35). If the result of malfunction determination by the malfunction determination unit 24 is inputted to the image generating unit 25, the image generating unit 25 also uses the result of the malfunction determination to generate the image data for the display screen 31. Then, the controller 23c determines whether the input unit 4 (termination instruction input unit 4a) has received an instruction to terminate detection of malfunctions from an operator (Step S37). If the input unit 4 has not received an instruction to terminate detection of malfunctions from an operator (NO in Step S37), the operation flow goes back to Step S31. If the input unit 4 has received an instruction to terminate detection of malfunctions from an operator (YES in Step S37), the device 100 for detecting a malfunction performs a predetermined near-final process and then terminates detection of malfunctions. In the predetermined near-final process, the image generating unit 25 receives the result of the frequency analysis (the amplitude data) at all of the times by the frequency analyzer 23a, then generates the three-dimensional image data for the result of the frequency analysis (the amplitude data) at all of the times, and transmits the image data to the HDD 22 (Step S39). Generation of the three-dimensional image data for the result of the frequency analysis at all of the times in this manner and transmission of the image data to the HDD 22 in the predetermined near-final process can result in reduction in the processing load for storage on the HDD 22 via the controller 23c, compared with a case in which the result of the frequency analysis is stored on the HDD 22 every time a result of frequency analysis is provided during the frequency analysis.

Now, the information-processing device 200 in FIG. 1 will be described. The information-processing device 200 includes a communication unit 201, a frequency analyzer 202, a determination unit 203, and a display unit 204. The communication unit 201 is a communication interface circuit that performs communication with, for example, the device 100 and the like for detecting a malfunction of a rotating machine connected to the network NW. The communication unit 201 functions as a receiver to receive the plurality of the sampled data sent by the communication unit 6 (more particularly, Data 1, Data 2, Data 3, Data 4, and so on in FIG. 3).

The frequency analyzer 202 analyzes the frequency of the plurality of the sampled data received by the communication unit 201. The frequency analyzer 202 performs the frequency analysis in the same manner as in the frequency analysis by the frequency analyzer 23a.

The determination unit 203 performs a secondary determination based on the result of the frequency analysis by the frequency analyzer 202. The secondary determination is more computationally intensive than the primary determination described above (the determination unit 203, for example, identifies the location of contact between rotors, if any). The technique for identifying the location of the contact based on the result of the frequency analysis is disclosed in, for example, Japanese Patent Application No. 2014-185819.

The frequency analyzer 202 and the determination unit 203 are constituted by hardware such as CPU, ROM, and RAM and software such as a program to perform the functions of the frequency analyzer 202 and the determination unit 203. As the determination unit 203 performs the secondary determination, which are more computationally intensive than the primary determination, the CPU in the information-processing device 200 has a performance that is better than the CPU in the device 100 for detecting a malfunction of a rotating machine.

The display unit 204 displays the result of the secondary determination. For example, if the rotors are in contact with each other, the display unit 204 displays the location of the contact. The display unit 204 is constituted by, for example, a liquid-crystal display.

Now, the major effects of the embodiment will be described. In the embodiment, the device 100 for detecting a malfunction of a rotating machine displays, in chronological order and in real time, the result of frequency analysis of sampled data created by sampling and detecting vibration of the rotating machine 5. In other words, the device 100 displays the operating states of the rotating machine 5 at respective times substantially in real time, which allows an operator to recognize a change in operation states of the rotating machine 5 over time, thereby allowing early detection of a malfunction of the rotating machine 5.

In the above embodiment, the malfunction determination unit 24 in the device 100 for detecting a malfunction of a rotating machine performs a primary determination about a malfunction of the rotating machine 5, while the determination unit 203 in the information-processing device 200 performs a secondary determination that is more computationally intensive than the primary determination. As the malfunction determination unit 24 performs the primary determination but does not perform the secondary determination, the malfunction determination unit 24 can be relatively less computationally intensive. This allows use of a simplified and reduced-size element such as hardware for the arithmetic processing unit 2. More particularly, the CPU for the arithmetic processing unit 2 can be CPU for mobile terminals or embedded CPU (for example, a microcomputer or FPGA (field programmable gate array) chip). Such configuration can also eliminate the need for disposing a large-sized cooling mechanism in the device 100 for detecting a malfunction of a rotating machine. Thus, according to the embodiment, the size of the device 100 for detecting a malfunction of a rotating machine can be reduced, which can make the device portable.

Although the amplifier 11a, the amplifier 11b, and the sampler 12 are disposed outside of the arithmetic processing unit 2 in the above embodiment, these elements may be disposed in the arithmetic processing unit 2. Although the input unit 4 receives an instruction to terminate detection of malfunctions from an operator before storing, on the HDD 22, an image data that shows the result of frequency analysis and that is generated by the image generating unit 25 in the above embodiment, the frequency analyzer 23a may store the result of the frequency analysis on the HDD 22 every time the result of frequency analysis is provided (as shown by the dashed arrow in FIG. 1). In this case, after the frequency analyzer 23a receives a sampled data Da from the detecting unit 1 (via the memory 21), the frequency analyzer 23a may start storing the result of frequency analysis on the HDD 22. In the above embodiment, the control and arithmetic unit 23 may be configured to execute a malfunction detection program stored in ROM so that elements such as the malfunction determination unit 24 and the image generating unit 25 are functionally configured with the control and arithmetic unit 23.

What is claimed is:

1. A device for detecting a malfunction of a rotating machine, the device comprising
    a detecting unit for detecting vibration of the rotating machine, sampling and detecting the vibration with a predetermined sampling frequency, and outputting, at a time at intervals of a predetermined period, a plurality of the sampled data detected within the predetermined period,
    a storage for storing the plurality of the sampled data outputted by the detecting unit,
    a frequency analyzer for analyzing the frequency of the plurality of the sampled data outputted by the detecting unit,
    a determination unit for performing a primary determination based on the result of the frequency analysis by the frequency analyzer,
    a display unit for displaying the result of the frequency analysis by the frequency analyzer in chronological order and in real time, and
    a transmitting unit for transmitting the plurality of the sampled data outputted by the detecting unit to an information-processing device for performing a secondary determination.

2. The device for detecting a malfunction of a rotating machine according to claim 1, wherein the frequency analyzer analyzes the frequency of the plurality of the sampled data by fast Fourier transform and outputs amplitude data corresponding to the respective frequencies.

3. The device for detecting a malfunction of a rotating machine according to claim 2, wherein the display unit displays the result of the frequency analysis of the sampled data at respective times in chronological order, in real time, and in three dimensions: the frequency dimension, the amplitude dimension (the amplitude dimension indicating amplitudes corresponding to respective frequencies), and time dimension.

4. The device for detecting a malfunction of a rotating machine according to claim 1,
    wherein the frequency analyzer initiates the frequency analysis when the frequency analyzer has received the plurality of the sampled data from the detecting unit, and
    wherein the analysis period from the initiation of the frequency analysis to the end of the frequency analysis is shorter than the predetermined period.

5. The device for detecting a malfunction of a rotating machine according to claim 1,
    wherein the storage initiates storage of the plurality of the sampled data and the result of the frequency analysis when the storage has received the plurality of the sampled data from the detecting unit, and wherein the storage period from the initiation of storage of the plurality of the sampled data to the end of the storage is shorter than the predetermined period.

6. The device for detecting a malfunction of a rotating machine according to claim 1,
wherein the device further comprises a termination instruction input unit for receiving an instruction to terminate detection of malfunctions,
wherein when the termination instruction input unit has received the instruction, the frequency analyzer reads all of the plurality of the sampled data stored in the storage, then analyzes the frequency of the data, and stores the result of the frequency analysis in chronological order in the storage.

7. The device for detecting a malfunction of a rotating machine according to claim 5,
wherein the frequency analyzer is functionally configured with a processor by executing a predetermined frequency-analysis-program, and
wherein upon starting the frequency analysis, the frequency analyzer is functionally configured with the processor, while upon completing the frequency analysis, the frequency analysis is cleared from the processor.

8. The device for detecting a malfunction of a rotating machine according to claim 1,
wherein the detecting unit comprises
a sensor for detecting vibration of the rotating machine and outputting a signals indicative of the detected vibration,
an attachment part for removably attaching the sensor to the rotating machine, and
a sampler for sampling the signal that is indicative of the vibration and is outputted by the sensor with a predetermined sampling frequency and outputting, at a time at intervals of the predetermined period, the plurality of the sampled data detected within the predetermined period.

9. The device for detecting a malfunction of a rotating machine according to claim 1,
wherein the device further comprises a battery receptacle for holding a battery that is a power source for actuating the device.

10. The device for detecting a malfunction of a rotating machine according to claim 1,
wherein the detecting unit comprises
a sensor for detecting vibration of the rotating machine and outputting a signal indicative of the detected vibration,
an attachment part for removably attaching the sensor to the rotating machine, and
a sampler for sampling a signal that is indicative of the vibration and is outputted by the sensor with a predetermined sampling frequency and outputting, at a time at intervals of the predetermined period, the plurality of the sampled data detected within the predetermined period, and
wherein the device further comprises
a battery receptacle for holding a battery that is a power source for actuating the device,
a notification unit for providing an optical indication when the determination unit has determined that the rotating machine has a malfunction,
an input unit for providing an input for operating the device, and
a housing for enclosing the storage, the frequency analyzer, the determination unit, the display unit, the transmitting unit, the sampler, the battery receptacle, the notification unit, and the input unit.

11. A system for detecting a malfunction of a rotating machine, the system comprising
a device for detecting a malfunction of a rotating machine, the device comprising a detecting unit for detecting vibration of the rotating machine, sampling and detecting the vibration with a predetermined sampling frequency, and outputting, at a time at intervals of a predetermined period, a plurality of the sampled data detected within the predetermined period, a storage for storing the plurality of the sampled data outputted by the detecting unit, a frequency analyzer for analyzing the frequency of the plurality of the sampled data outputted by the detecting unit, a determination unit for performing a primary determination based on the result of the frequency analysis by the frequency analyzer, a display unit for displaying the result of the frequency analysis by the frequency analyzer in chronological order and in real time, and a transmitting unit for transmitting the plurality of the sampled data outputted by the detecting unit, and
an information-processing device that comprises a receiver for receiving the plurality of the sampled data transmitted by the transmitting unit, a second frequency analyzer for analyzing the frequency of the plurality of the sampled data received by the receiver, and a second determination unit for performing a secondary determination based on the result of the frequency analysis by the second frequency analyzer.

* * * * *